United States Patent [19]

Barreras

[11] Patent Number: 5,591,217
[45] Date of Patent: Jan. 7, 1997

[54] IMPLANTABLE STIMULATOR WITH REPLENISHABLE, HIGH VALUE CAPACITIVE POWER SOURCE AND METHOD THEREFOR

[75] Inventor: Francisco J. Barreras, Miami, Fla.

[73] Assignee: Plexus, Inc., Miami, Fla.

[21] Appl. No.: 368,326

[22] Filed: Jan. 4, 1995

[51] Int. Cl.$^6$ .................................................... A61N 1/18
[52] U.S. Cl. .................................................... 607/61
[58] Field of Search .............................. 607/5, 9, 32, 34, 607/65, 2, 33, 61

[56] References Cited

U.S. PATENT DOCUMENTS

| | | | |
|---|---|---|---|
| 3,209,081 | 9/1965 | Ducote et al. ........................... | 179/107 |
| 3,258,013 | 6/1966 | Druz . | |
| 4,102,344 | 7/1978 | Conway et al. . | |
| 4,406,288 | 9/1983 | Horwinski et al. . | |
| 4,408,607 | 10/1983 | Maurer . | |
| 4,408,608 | 10/1983 | Daly et al. . | |
| 4,424,812 | 1/1984 | Lesnick . | |
| 4,556,061 | 12/1985 | Barreras et al. . | |
| 4,612,934 | 9/1986 | Borkan . | |
| 4,690,144 | 9/1987 | Rise et al. . | |
| 4,702,254 | 10/1987 | Zabara . | |
| 5,312,439 | 5/1994 | Loeb ......................................... | 607/2 |
| 5,324,316 | 6/1994 | Schulman et al. ........................ | 607/61 |
| 5,358,514 | 10/1994 | Schulman et al. ........................ | 607/61 |
| 5,405,367 | 4/1995 | Schulman et al. ........................ | 607/61 |

OTHER PUBLICATIONS

Pacing and Clinical Electrophysiology, Aug. 1988, vol. 11, No. 8, pp. 1117–1247.
Panasonic Technical Guide of Electric Double Layer Capacitors.

*Primary Examiner*—William E. Kamm
*Assistant Examiner*—Scott M. Getzow
*Attorney, Agent, or Firm*—Robert C. Kain, Jr.

[57] ABSTRACT

The implantable stimulator in accordance with the principles of the present invention utilizes a high value, small sized capacitor having at least a capacitive rating of 0.1 farads which is completely contained within the implantable stimulator. This high value, small size capacitor or series of capacitors enables the implantable stimulator to deliver, on a controlled and continual basis, electric stimulation pulses to targeted tissues over at least a 8 period. Further, the capacitive power source is recharged or replenished via an external, RF coupled device on a daily or other long term periodic basis. The method includes providing, on an exclusive basis, power to an implantable stimulator via a high value capacitive source during at least a twenty-four cycle of substantially continual delivery of electric stimulation pulses to targeted tissue. The method includes incorporating and containing a capacitive device in the implantable stimulator wherein the capacitive device has a capacitive rating of at least 0.1 farads. The capacitive device captures and stores a pre-determined amount of coulombs of electrical energy. This electrical energy is utilized to power the implantable stimulator during the 8 hour cycle during substantial continual delivery of electric stimulation pulses, all based upon energy stored by the capacitive device.

25 Claims, 3 Drawing Sheets

IMPLANTABLE STIMULATOR WITH REPLENISHABLE, HIGH VALUE CAPACITIVE POWER SOURCE AND METHOD THEREFOR

The present invention relates to an implantable stimulator which includes a high value capacitive power source (exceeding 0.1 farads) and a method to power the implantable stimulator on an exclusive basis during continual delivery of electrical stimulation pulses.

BACKGROUND OF THE INVENTION

Implantable tissue stimulators are utilized to deliver a train of low voltage level electrical pulses to specific nerves or muscles via an implanted lead. Implantable stimulators have been utilized to stimulate nerves in the spinal cord (paresthesia), to stimulate the bladder and control bladder functions, to stimulate the sphincter in control of that bodily function, and to stimulate the brain (for example, to control epileptic episodes). Other implantable devices provide diagnostic monitoring of a patient's condition as well as the delivery of drugs subcutaneously (such as an insulin pump).

With respect to spinal control stimulation nerves in the spinal cord are electrically stimulated with low voltage level, controlled electric current pulses delivered directly on or at the nerve via an implanted lead or leads in order to achieve paresthesia. Spinal cord stimulation is utilized to treat chronic pain of the trunks and limbs as well as for intractable chest angina. For example, spinal cord stimulation has been utilized to treat peripheral vascular disease (PVD).

With respect to all of these implantable stimulators and devices, it is necessary to provide power to the device implanted below the skin. Since the device is subcutaneously implanted in a patient, the power source must support stimulator or device operation for a reasonable period of time in order to reduce further surgical trauma to the patient. If the device cannot operate under its own power, the device must be surgically removed to replace or recharge the power source therein.

Stimulators can be classified in three general areas: radio frequency or RF coupled and powered stimulators, battery powered stimulators and stimulators which combine RF coupling and battery powered systems. The term battery means an electrochemical (primary or secondary) power system.

The RF coupled and powered stimulator does not carry or contain an independent power source. Therefore, the RF coupled stimulator requires an external RF transmitter and a surgically implanted receiver. The RF link transfers stimulation pulses percutaneously through the skin and adjacent tissue layers of the patient from the external RF transmitter to the surgically implanted RF receiver and stimulator device. The transmitter sends stimulation pulses to be applied ultimately to the implanted electrodes plus programming data defining the polarity of each electrode relative to each other to the implanted stimulation device. The implanted receiver obtains these stimulation pulses and programming data, converts the pulses as necessary, delivers the energy contained in each transmitted stimulation pulse to the implanted electrodes as defined by the programming data. The stimulation pulses are inductively coupled emf waves from the external transmitter to the implanted receiver. The common disadvantage of the RF coupled and powered stimulator is that the patient must always wear the external transmitter and antenna (even during sleep) in order for the implanted receiver to deliver stimulation pulses to the targeted tissue. Stimulation therapy ceases the moment the transmitter antenna is withdrawn just a few inches away from the implanted receiver. Although the RF powered and coupled stimulator has this disadvantage, the service life of such an RF coupled and powered stimulator is not limited to the life of a battery contained within a fully implantable stimulation unit. Accordingly, the long term cost of the RF coupled and powered stimulators is less than the battery powered stimulators because the service life of the former is much longer than that of the latter. RF coupled and powered stimulators have been commercially marketed by Medtronics of Minneapolis, Avery laboratories of New York and Neuromed of Fort Lauderdale, Fla.

The battery powered stimulator utilizes a primary, non-rechargeable battery as a power source to power the implanted stimulator. This battery will operate without requiring an external transmitter to recharge or replenish the battery in the implantable stimulator. The battery provides sole and exclusive power to the implanted stimulator continually while the stimulator generates one or more electric stimulation pulses, in a controlled manner, to the target tissue. Of course, the stimulation pulses are delivered to the targeted tissue via implanted leads. An external programmer may be used to non-invasively adjust the stimulation parameters or control values in the implanted stimulator. Programming may be provided through an RF telemetry link. After programming, the stimulator remembers the parameter values (the values are stored in an electronic memory) as long as the battery voltage remains above a minimum voltage level required by the electronics. Unfortunately, the service life of these battery powered stimulators is limited to the battery life. Accordingly, it is necessary to surgically remove and then replace the battery powered implantable stimulators upon depletion of the electrochemically active materials in the battery. This disadvantage (i.e. surgical replacement) increases its long term cost to the patient relative to the aforementioned RF coupled and powered stimulators. The battery powered implantable stimulators do not require an external transmitter to deliver the stimulation electrical pulses. Accordingly, the battery powered implantable stimulators are easier to use and more comfortable than the RF coupled and powered stimulators. Battery powered stimulators have been marketed by Medtronics of Minneapolis, Neuromed of Ft. Lauderdale and Exonix of Miami.

The third category of implantable stimulators include stimulators which combine the RF coupling and powered delivery systems with the battery powered implantable stimulator technology. These types of stimulators enable the patient to carry the implantable stimulator without the necessity of having an external RF coupled unit proximate the implant at all times. However, the stimulator must be surgically replaced after the battery is depleted if use of the external RF transmitter is not desired. This type of stimulator allows RF coupled stimulation at times when wearing the external transmitter is not objectionable, thereby extending battery life. Also, this type of stimulator may allow for continuing RF coupled stimulation after the internal power source is depleted, although some of these RF coupled and battery powered implantable stimulators do not operate if the battery is completely depleted in the implanted stimulator.

U.S. Pat. No. 4,612,934 to Borkan discloses a non-invasive multi-programmable tissue stimulator. The Borkan implantable stimulator includes an external transmitter which transfers power percutaneously through an RF coupling to an implanted stimulator. The implanted stimulator does include a voltage storage circuit and a battery. The voltage storage circuit stores a minimal amount of voltage and electrical energy. Particularly, the Borkan disclosure provides "[t]he output of the detector circuit 22 is stored as voltage Vm in the voltage storage circuit 36 which comprises diode 80, capacitor 82, optional zener diode 83 and resistor 84. Alternatively, a rechargeable voltage source could be substituted for capacitor 82." Column 14, lines 5–9. Obviously, capacitor 82 is used as a filter device and not as a power source. The long term voltage stored in this circuit Vm is applied to a comparator and, when voltage Vm is less than a predetermined reference voltage, the implantable stimulator "goes to sleep," that is, the implantable stimulator stops delivering stimulation pulses to the targeted tissue. The implantable stimulator is "woken up" or activated upon receipt of RF coupled commands in a certain sequence. Accordingly, the voltage storage circuit in the Borkan disclosure simply acts as a temporary voltage storage unit to detect the presence of the RF transmitter and not a long term power supply for the implanted stimulator. The Borkan stimulator is utilized to stimulate tissue for various neurological and muscular disorders.

U.S. Pat. No. 4,690,144 to Rise discloses a wireless transcutaneous electrical tissue stimulator which deliver stimulation pulses to the surface of the patient's skin. It appears that the Rise transcutaneous stimulator is battery powered stimulator controlled by a wireless remote control. The Rise transcutaneous tissue stimulator is utilized to relieve pain and stimulate muscles as necessary.

U.S. Pat. No. 4,424,812 to Lesnick discloses an implantable, externally programmable, microprocessor-controlled tissue stimulator. The Lesnick disclosure does not describe in detail the electrical energy storage device in the implanted stimulator. However, it is apparent that an internal battery is utilized within the Lesnick implantable stimulator. The external RF coupled device is utilized only to program the implantable stimulator. The patient turns on and off the implanted stimulator by placing and removing a hand held magnet which in turn opens and closes a reed switch in the implantable stimulator.

U.S. Pat. No. 4,406,288 to Horwinski discloses a bladder control device and a method therefor. Basically, an implantable stimulator is utilized to stimulate the pelvic muscles and to control the bladder. The implantable stimulator uses a internal battery as an energy storage device.

U.S. Pat. No. 4,702,254 to Zabara discloses a neurocybernetic prosthesis. The preferred embodiment incorporates a battery and associated circuitry in a fully implantable enclosure. An RF coupled powered device is also discussed.

U.S. Pat. No. 4,556,061 to Barreras discloses a cardiac pacer with a battery consumption monitor circuit. This pacing unit, embodied as an implantable stimulator of the heart, utilizes a battery.

OBJECTS OF THE INVENTION

It is an object of the present invention to provide an implantable stimulator with a replenishable, high value capacitive power source. Capacitors do not suffer a significant wear out during charge and discharge cycles as rechargeable batteries do.

It is another object of the present invention to provide a method of supplying power, on an exclusive basis, during at least an 8 hour cycle of substantially continually delivery of electric stimulation pulses utilizing a high value capacitor.

It is a further object of the present invention to provide an implantable stimulator which can be operated for a significant period of time using the energy stored in a high value capacitor (exceeding 0.1 farads).

It is a further object of the present invention to provide an implantable stimulator with a capacitive power source utilizing a plurality of high value capacitors electrically connected in parallel.

It is a further object of the present invention to utilized this high value capacitive power source in combination with an implantable stimulator.

It is further object of the present invention to non-invasively fully replenish the capacitive power source within 30 minutes or less.

It is a further object of the present invention to utilize a high value capacitive power source in conjunction with diagnostic RF coupled data transmitter and receiver devices implanted in the patient.

It is another object of the present invention to provide a drug delivery system utilizing a replenishable, high value capacitive power supply.

SUMMARY OF THE INVENTION

The implantable stimulator in accordance with the principles of the present invention utilizes a high value, small sized capacitor having at least a capacitive rating of 0.1 farads which is completely contained within the implantable stimulator. This high value, small size capacitor or series of capacitors enables the implantable stimulator to deliver, on a controlled and continual basis, electric stimulation pulses to targeted tissues over at least an 8 hour period. Further, the capacitive power source is replenished via an external, RF coupled device on a daily or other long term periodic basis. During the replenishing cycle, the energy contained in the battery of the external transmitter is transferred to the internal capacitive power source in the implantable stimulator. The method includes providing, on an exclusive basis, power to an implantable stimulator via a high value capacitive source during at least an 8 hour cycle of substantially continual delivery of electric stimulation pulses to targeted tissue. The method includes incorporating and containing a capacitive device in the implantable stimulator wherein the capacitive device has a capacitive rating of at least 0.1 farads. The capacitive device captures and stores a predetermined amount of coulombs of electrical energy. This electrical energy is utilized to power the implantable stimulator during at least an 8 hour cycle during substantial continual delivery of electric stimulation pulses, all based upon energy stored by the capacitive device. Longer cycles (exceeding 24 hours) may be possible.

BRIEF DESCRIPTION OF THE DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENTS

The present invention relates to a method and an apparatus for an implantable stimulator with a replenishable, high value, capacitive power source. Particularly, this high value capacitive power source could be embodied as a single high value capacitor or a plurality of parallel connected high value capacitors. One type of high value, small size capacitors is sold by Panasonic as Model No. 641. The Panasonic capacitor has a diameter of approximately 18 millimeters and a thickness of approximately 4 millimeters. Accordingly, these capacitors have a volumetric size of less than 4.0 cubic centimeters. This Panasonic model capacitor has a capacitive rating of 1.0 farads. The typical size of the implantable stimulators is 5 centimeters by 6 centimeters by 2 centimeters (that is, 60 cubic centimeters). The benefit of using these high value, small size capacitive energy storage units is that the energy storage is not an aqueous or water-based system.

Prior art implantable stimulators utilize nickel-cadmium rechargeable batteries. These batteries store energy in an aqueous system and the energy storage mechanism is an electrochemical reaction. Further, these nickel cadmium batteries release hydrogen gas which adversely affect the performance of the stimulator and compromise the patient's well being.

The high value, small sized capacitive energy storage source utilized in the present invention are small, light weight and chemically inert. Further, the electrical storage mechanism is a physical phenomena and not electrochemical reaction as is the case with nickel cadmium batteries or other rechargeable batteries.

These capacitors are classified as low internal impedance, low power loss and high charge rate capacitors.

Figure 1:
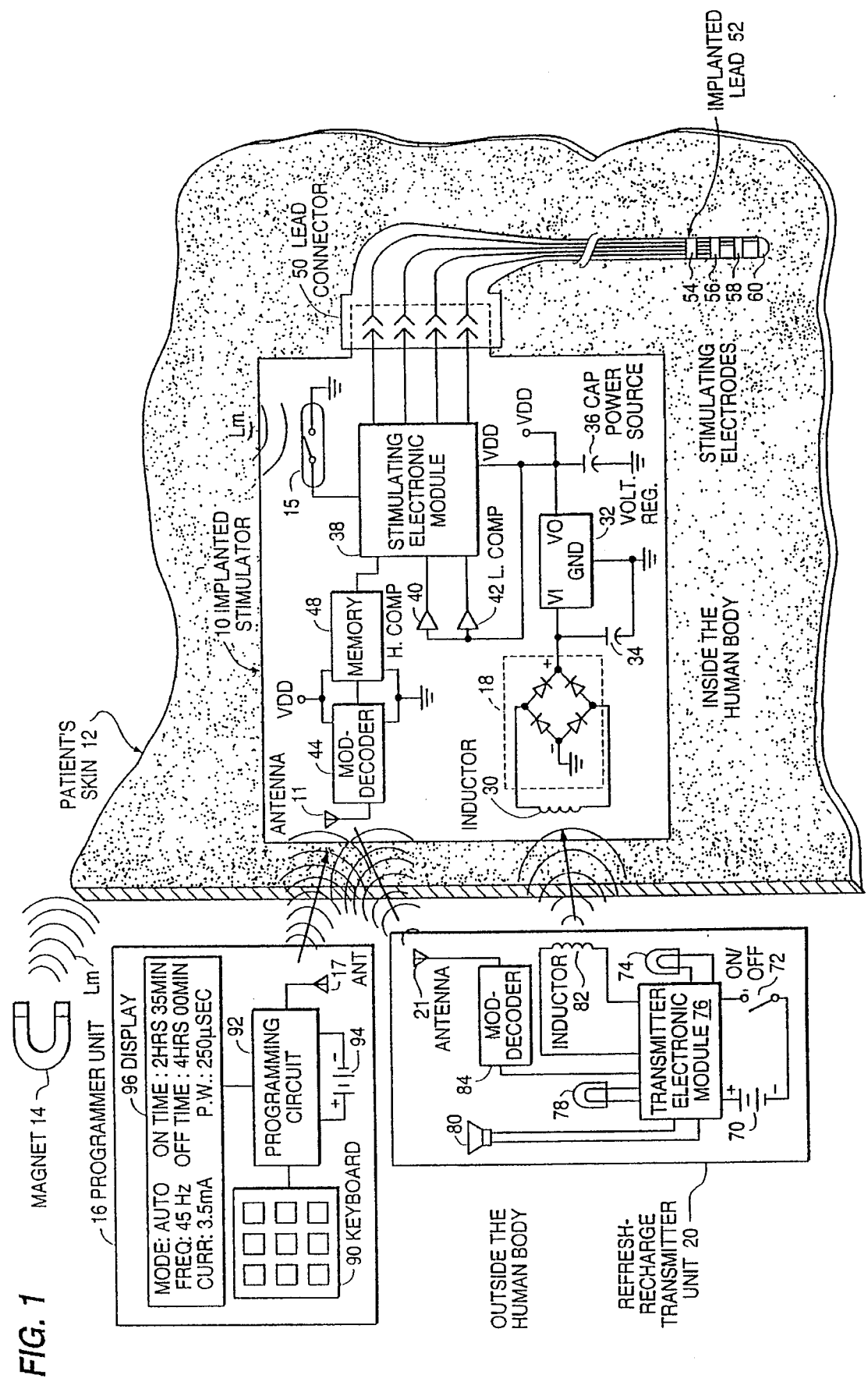
FIG. 1 diagrammatically illustrates the implanted stimulator, the hand held magnet (patient control), the programmer unit (RF coupled to the implanted stimulator) and the refresh-recharge transmitter unit (RF coupled to stimulator)

FIG. 1 illustrates stimulator 10 implanted subcutaneously with respect to a patient's skin 12. A magnet 14 is utilized by the patient to deliver electromagnetic force waves (EMF waves) identified in FIG. 1 as waves Lm. These EMF waves Lm open and close a reed switch 15 mounted within the casing of implantable stimulator 10. The magnet is used by the patient to start/stop stimulation. As stated earlier, the implantable stimulator occupies approximately 60 cubic inches and is sized roughly 5 cm by 6 cm by 2 cm. FIG. 1 also illustrates a programmer unit 16 and a refresh-replenish transmitter unit 20. Programmer unit 16 and refresh-recharge transmitter unit 20 are coupled via radio frequency (RF) waves to the implantable stimulator 10. However, command signals from either programmer unit 16 or refresh-replenish transmitter unit 20 are sent and received via antennas 17 and 21, respectively. Preferably, refresh-recharge transmitter unit 20 is not used concurrently with programmer unit 16. In any event, an RF telemetric data link is established between antennas 17, 21 and internal antenna 11 in the implanted stimulator 10 when either the programmer unit 16 or refresh-recharge unit 20 is placed in close proximity to implanted stimulator 10.

The major components of implanted stimulator 10 include an inductor receiver coil 30, a full rectifier bridge 18 (consisting of a plurality of diodes) coupled to a voltage regulator 32. A small size capacitor 34 is utilized to smooth the input voltage VI input fed into voltage regulator 32. The output voltage VD of regulator 32 is applied to capacitive energy power supply and source 36 which establishes source power VDD. This source power is applied to stimulating electronic module 38, high threshold comparator 40, low threshold comparator 42, modulator/demodulator and decoder circuit 44 and memory unit or programmable device 48. The output of stimulating electronic module 38 is applied to lead connector 50 and lead connector 50 supplies electric stimulation pulses to implanted lead 52. In a preferred embodiment, implanted lead 52 has plurality of linear electrodes or terminals 54, 56, 58 and 60. Implanted lead 52 is placed on or near targeted tissue such as heart tissue, nerves in the spinal cord, muscles in the bladder or sphincter, or wherever electrical pulses are required to stimulate tissue.

Figure 6:
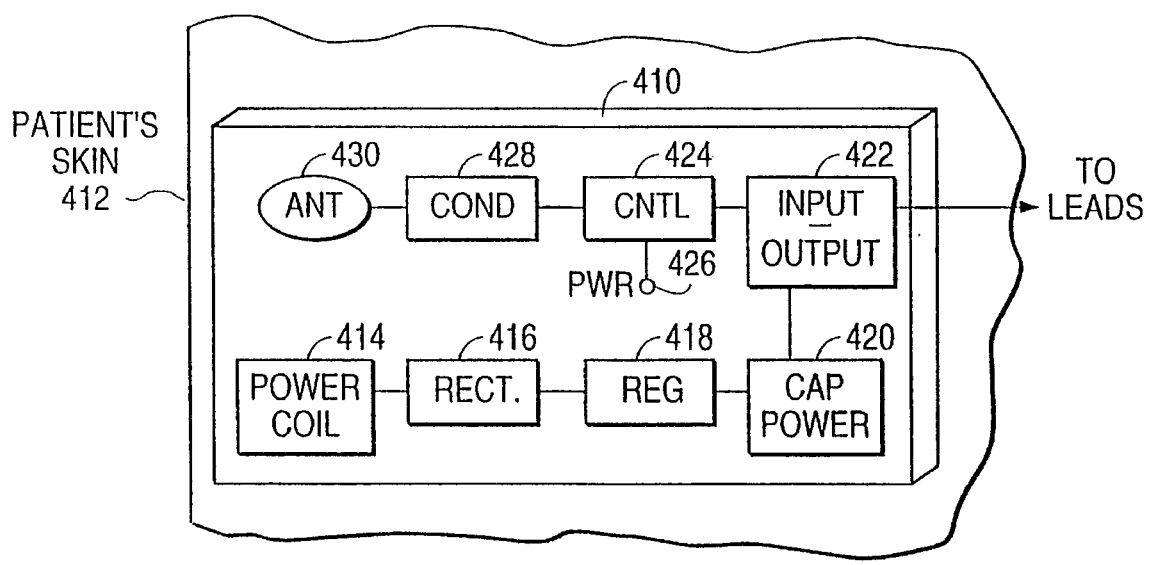

Alternatively, rather than stimulating tissue, an implantable diagnostic device could be utilized to detect the condition of certain bodily organs such as heart or brain. Also, a drug delivery system could be powered capacitive power source 36. In FIG. 6, the diagnostic module would replace stimulator module 422. The electronic pump would replace module 422 if the implant was a drug delivery system.

As described above, the capacitive power source 36 is a high value, small size capacitive energy device comprising a single capacitor or a plurality of serially connected capacitors having a capacitive rating of at least 0.1 farads and limited in volumetric size to less than 4.0 cubic centimeters.

The refresh-recharge transmitter unit 20 includes a primary battery 70, an ON/OFF switch 72, a low battery light or LED 74, a transmitter electronic module 76, a "stimulator full" light or LED 78, and audible alarm or speaker 80, an RF inductor power coil 82, a modulator/demodulator and decoder 84 and an antenna 21.

In operation, when rechargeable battery 70 is fully charged and ON/OFF switch 72 is on, the refresh-recharge transmitter unit 20 is placed in close proximity to skin 12 and implanted stimulator 10. Inductor coil 82 emits RF waves establishing EMF wave fronts which are received by inductor 30.

Further, transmitter electronic module 76 sends out command signals which are converted by modulator/demodulator decoder 84 and sent via antenna 21 to antenna 11 in the implanted stimulator. These received command signals are demodulated by decoder 44 and replied and responded to based on a program in memory 48. Memory 48 then activates the proper control and the inductor receiver coil 30 excepts the RF coupled power from inductor 82.

The RF coupled power, which is alternating current or AC in nature, is converted by the full bridge rectifier circuit 18 into a high DC voltage. Small value capacitor 34 operates to filter and level this high DC voltage at a certain level. Voltage regulator 32 converts the high DC voltage to a lower precise DC voltage while capacitive power source 36 refreshes and replenishes. In a preferred embodiment, approximately 5 coulombs are stored in capacitive power source 36. This is sufficient to power stimulating electronic module 38 for at least 8 hours during the delivery of substantially continual electric stimulation pulses to targeted tissues via implanted leads 52. Longer energy storage times, exceeding 24 hours, are possible dependent upon the value of the capacitor and the power drain due to the continual delivery of stimulation pulses.

When the voltage in capacitive power source 36 reaches a predetermined level (that is, VDD reaches a certain predetermined high level), the high threshold comparator 40 fires and stimulating electronic module 38 sends an appropriate command signal to memory 48. Memory 48 then sends an appropriate "fully charged" command through modulator/decoder 44 and antenna 11. This command signal indicating that capacitive power source 36 is fully charged, is received by antenna 21 in the refresh-recharge transmitter unit 20. This "fully charged" command signal is decoded by demodulator/decoder 84 and transmitter electronic module 76 then illuminates the "stimulator full" light or LED 78. Further, after a predetermined time period, the patient or user may hear an audible alarm generated by speaker or audio chip 80 in the refresh-replenish transmitter unit 20. At that point in time, the user turns off switch 72 which stops the production of RF power signals via conductor 82 percutaneously to inductor 30.

In the demand mode of operation, when the patient wants to turn ON the implanted stimulator, he or she places hand held magnet 14 near the implant. The magnet emits a magnetic force Lm which pulls reed switch 15 closed. Upon closure of reed switch 15, stimulating electronic module 38 in conjunction with memory 48 begins the delivery (or cessation as the case may be) of controlled electronic stimulation pulses to the targeted tissues near implanted leads 52. In the AUTO mode, stimulation is automatically delivered to the implanted lead based upon programmed ON/OFF times. In a single mode, stimulation is delivered only when the magnet is acting on the switch.

Figure 2:
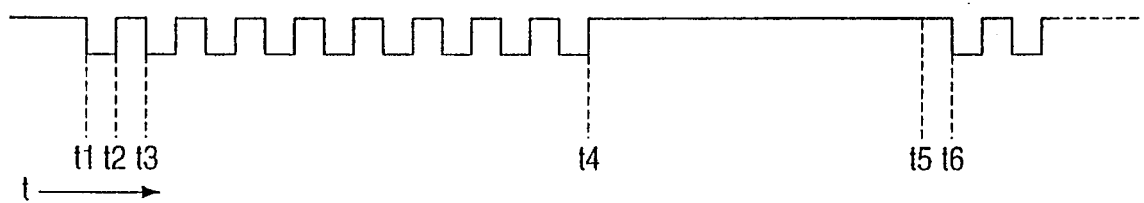
FIG. 2 diagrammatically illustrates a time line showing an example of the substantially continual delivery of stimulation pulses via the implanted stimulator.

FIG. 2 diagrammatically illustrates one type of controlled stimulation pulses. The pulses are classified by pulse width ($t_1$–$t_2$), pulse interval ($t_1$–$t_3$), and pulse amplitude (current level). One frequency cycle is measured from the leading edge of one pulse to the next pulse. Stimulating frequency (PPS) can be calculated by equation 1.

$$F = \frac{1}{\text{PulseInterval}} \qquad \text{Equation 1:}$$

The ON time for the entire stimulation pulse train is establish by period $t_1$ through $t_4$. Accordingly, memory 48 stores information regarding the pulse width, pulse amplitude and stimulating frequency, for the delivery of substantially continual stimulation pulses. The patient determines the total ON time identified as time period $t_1$–$t_4$ in FIG. 2. For example at time $t_5$, the patient places magnet 14 near implanted stimulator 10. This closes reed switch 15 and at time $t_6$, the stimulation pulses begin again. Of course, it is important that the physician or medical technician be permitted to change the pulse current frequency, pulse width, and ON time of the electric stimulation pulses. This is accomplished with programmer unit 16.

Returning to FIG. 1, programmer unit 16 includes keyboard 90, programming circuit 92, rechargeable battery 94 and display 96. Display 96 may include the following elements:

DISPLAY TABLE

Mode: Automatic-On Demand-Off
Frequency: Hz (range $n_1$ Hz, to $n_2$ Hz)
Current: mA (range $m_1$ mA to $m_2$ mA)
On Time: minutes maximum
Off Time: minutes maximum
Pulse Width: microseconds The physician or medical technician programs programmer unit 16 via keyboard 90. This program regarding the frequency, pulse width, ON time etc. is stored in programming circuit 92. Rechargeable battery 94 enables this programmer unit to be portable. Portability is necessary because antenna 17 in within programmer unit 16 must be placed relatively close to implanted stimulator 10 in order to transfer the commands and programming information from antenna 17 to antenna 11. Upon receipt of this programming data, modulator/demodulator and decoder 44 decodes and conditions these signals and the digital programming information is captured by memory 48. This digital programming information is further processed by stimulating electronic module 38.

As stated earlier, in the demand operating mode, after programming the implanted stimulator, the patient turns ON and OFF the implanted stimulator via hand held magnet 14 and a reed switch 15. In the automatic mode the implanted stimulator turns ON and OFF automatically according to the programmed values for the ON and OFF times.

In one embodiment, the capacitive power source 36 can be recharged or replenished within approximately one hour via the refresh-replenish transmitter unit 20. After the capacitive power source 36 is fully charged, the capacitive power source will enable stimulating electronic module 38 to operate for at least 8 hours before further recharging is necessary. Twenty-four hour operation without recharging or refreshing the capacitive power source is the preferred embodiment. Therefore, since capacitive power source 36 is not subject to "memory loss" common with nickel cadmium rechargeable batteries and not subject to out gassing of obnoxious fumes (common with nickel cadmium batteries), the present invention provides for long service life and lower therapy cost than other comparable implanted stimulators. Further, the patient can easily utilize the implanted stimulator because it is not necessary to continually wear the RF coupled external transmitter for the implanted stimulator to work.

The number of replenish cycles for the capacitive power source 36 and particularly the Panasonic capacitor Model No. 461 is an excess of 100,000 cycles. This exceeds the typical recharge cycle life of a nickel cadmium batteries or other rechargeable chemical battery systems of 500 cycles.

In a preferred embodiment, stimulating electronic module 38 in memory 48 are configured as CMOS units. These components result in a low voltage drain based on the operation of these electronic devices.

When the value of the power source VDD generated by capacitive power source 36 reaches a low level, low threshold comparator 42 fires. This causes stimulating electronic module 38 to go into a "sleep" or wait mode. During the sleep or wait mode, stimulating electric pulses are not delivered to implanted leads 52. The implanted stimulator is "woken up" when refresh-recharge transmitter unit 20 is placed in close proximity to stimulator 10. During this replenish cycle, wake up commands are sent via antenna 21 to antenna 11 and stimulating electronic module 38 is woken up. Simultaneously, as soon as voltage regulator 32 develops an output voltage VDD which exceeds low threshold comparator value 42, the implanted stimulator can immediately begin delivering electric stimulating pulses to the targeted tissue. This ability to replenish and simultaneously deliver stimulating pulses to targeted tissues is unique with respect to the present invention.

The operating principles of an implantable primary or secondary battery powered device and an implantable device powered by a high value capacitive power source are very different. A battery generates energy in a chemical reaction. This energy release or energy storage is accomplished by having two chemically active materials with different electrode potentials present inside the battery. One material serves as the anode which readily gives up electrons and is thus oxidized. Batteries for implantable applications usually employ lithium metal as the anode. The second electrochemically active material in a battery acts as the cathode which accepts electrons and is therefore chemically reduced. Typical implantable battery cathode materials are iodine, silver vanadium oxide, carbon monofluoride and cupric sulfide. External to the battery, transfer to ions between anode and cathode is made possible by the electrolyte which provides high ionic conductivity, but little or no electronic conductivity. A porous separator between the cathode and anode may be used in some batteries to prevent mechanical contact between the anode and the cathode, while allowing electrolyte and ion flow. As a load is applied to the battery, both lithium anode and cathodic material are chemically converted (reacted) to produce a resultant electrical energy until complete depletion of the active materials is achieved. At this point a primarily battery is rendered useless.

In the case of rechargeable battery, both anode and cathode material are recovered back to their original state by recharging the battery. Battery chemistries that are rechargeable are said to have a "reversible reaction." Rechargeable batteries have a limited life since upon recharge, both cathodic and anodic materials are eventually affected. These batteries give off hydrogen upon either charge or discharge, may suffer from a "memory effect" and could explode if shorted. Unlike high value capacitance devices, all rechargeable batteries produce electricity as a result of a chemical reaction. In other words, energy is the by-product of an electrochemical reaction. The general chemical reaction of a nickel-cadmium rechargeable battery is described below in Equation 2.

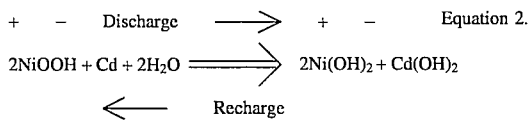

Equation 2.

In the high value capacitance power source utilized in the present invention, the principles of operation are purely physical. No chemical reactions are necessary to obtain electrical energy. For example, in a high value capacitance device model such as a double layer capacitor, the charged particles and oriented dipoles that form at the interface of any two phases (solid/solid, solid/liquid, etc.) form a capacitance effect such that the application of an electric field (charge) results in an accumulation of electrostatic charges in a double layer. In essence, the high value capacitance power source serves as an energy storage tank without altering its chemical composition. This principle is defined in the Panasonic product specification for Model 461. It is a pure physical phenomena.

This product specification demonstrates the non-chemical principle of storing and discharging electrical energy. In a high value capacity power source such as the electric double layer capacitors, the electrode material yields a high surface area of around 1000 $m^2$/gram which accounts for it high volumetric efficiency of over 3 farads per cubic inch. Further, unlike batteries the electrodes are non-polar since they are both typically constructed from inert activated carbon mesh. The activated carbon and electrolyte are chemically passive during either charge or discharge mode, hence no chemical reactions or by-products are generated. In addition, the high capacitance power source is safer than batteries since they will not explode or be damaged if short circuited. Unlike conventional electrochemical batteries, the high value capacitance power devices will not manifest anomalies such as charge memory, gas evolution, reactive chemicals, parasitic reactions, heat generation and electrolyte starvation. High value capacitance power sources provide virtually unlimited service life since their electrode system is inert and resistant to electrochemical wear out.

Figure 3:
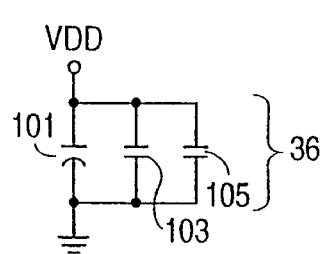
FIG. 3 diagrammatically illustrates one embodiment of the high value, small size capacitive energy storage unit consisting of a plurality of parallel connected capacitors.

FIG. 3 illustrates that capacitive power source 36 can be configured as a plurality of parallel connected capacitors 101, 103 and 105.

Figure 4:
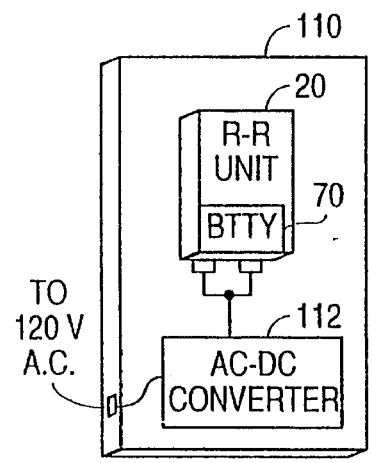
FIG. 4 diagrammatically illustrates a replenish unit for the refresh-recharge transmitter unit.

FIG. 4 diagrammatically illustrates a recharger and an AC-DC converter unit 110 for refresh-replenish unit 20. The refresh-replenish transmitter unit 20 may operate with a rechargeable or primary battery 70 (FIG. 1). This rechargeable battery may be nickel cadmium or other typical recharging battery. However, this rechargeable battery must be periodically recharged. This is accomplished by AC-DC recharging unit 110. Unit 110 is electrically connected to a 120 volt alternating current (AC) power source. Essentially, this 120 volt AC power is converted via converter 112 into a DC voltage. The output of AC-DC converter unit 112 is a DC power signal which is fed to rechargeable battery 70 in the refresh-recharge transmitter unit 20.

Figure 5:
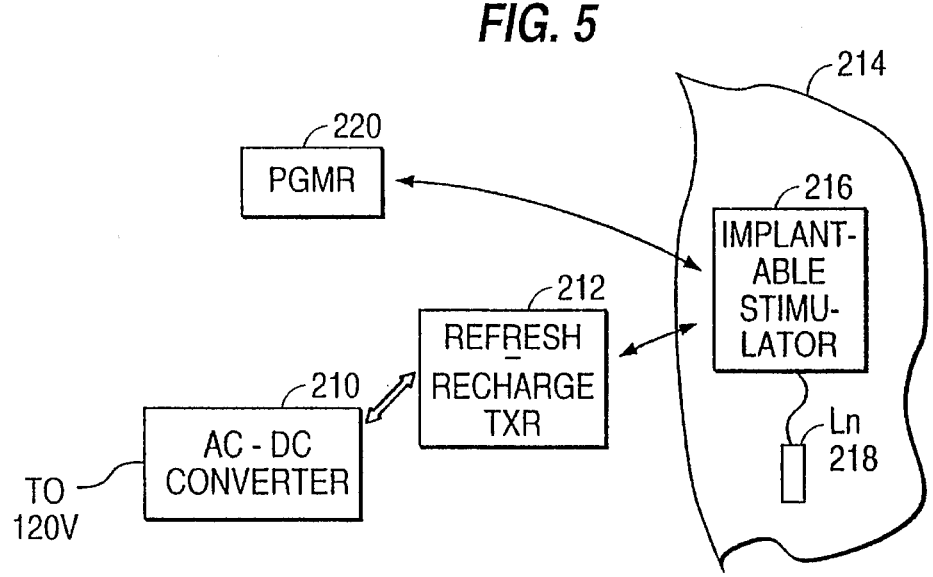
FIG. 5 diagrammatically illustrates the external programmer, external refresh-recharge transmitter, AC-DC converter for the refresh unit and the implanted stimulator; and, FIG. 6 diagrammatically illustrates the major components of the stimulators and other implantable devices.

FIG. 5 diagrammatically illustrates the operation of the present invention in block diagram form. AC-DC converter unit 210 is commonly electrically connected to a 120 volt AC power source. Refresh-replenish transmitter unit 212 is placed in a cradle in the AC-DC converter 210 or is removed therefrom. Upon removal, the refresh-replenish transmitter unit 212 is placed close to skin 214 of the patient. The implantable stimulator 216 then is begins to accept RF coupled power as described above with respect to inductors 82 and 30. Implantable electrodes Ln 218 are placed during surgery next to targeted tissue. When the implanted stimulator 216 must be programmed by the doctor or medical technician, programming unit 220 is placed near skin 214. The programming commands are sent via telemetry to the memory and programmable devices incorporated within implantable stimulator 10.

FIG. 6 diagrammatically illustrates the implantable stimulator in block diagram form. The implantable stimulator 410 is subcutaneously placed in the patient during a surgical procedure. The implantable stimulator 410 is entirely beneath the patient's skin 412. The stimulator includes a power reception coil 414, a full wave rectifier 416, a voltage regulation device 418 and a capacitive power source 420. The inductor power coil, rectifier (rect.) and voltage regulator are necessary to convert the RF coupled power to a constant DC voltage equal to the maximum rated voltage of high value capacitors 420. The output power from capacitive power source 420 is provided to input/output circuit 422. As stated earlier, these stimulators may be neuro stimulators, pacemakers or may be part of a drug delivery system or an RF coupled diagnostic unit. In the event an RF coupled diagnostic unit is utilized, the diagnostic unit would not necessarily stimulate the targeted tissue but rather monitor the electrical activities of that targeted tissue. For example, monitoring EEG and EKG signals is possible. Diagnostic data is obtained from the implant via telemetry.

Implanted device 410 further includes control programming electronics 424 which are further fed with power 426. Power 426 is supplied by capacitive power source 420. A conditioner circuit 428 is interposed between controlled electronics 424 and telemetry antenna 430.

The claims appended hereto are meant to cover modifications and changes within the spirit and scope of the present invention.

What is claimed is:

1. A system for delivering, in a controlled manner, one or more electric stimulation pulses to targeted tissue comprising:

an implantable stimulator, said stimulator capable of delivering, in a controlled manner, one or more electric stimulation pulses to targeted tissue;

a power source, contained within said implantable stimulator, sufficient to supply power to said implantable stimulator on an exclusive basis over at least an 8 hour period, said power source including a high value, small size capacitive energy storage unit having a capacitive rating of at least 0.1 farads; and an inductor coil adapted to gather emf power transmissions, a rectifier and a voltage regulator, all electrically coupled to said capacitive energy storage unit and incorporated into said implantable stimulator, for supplying replenishing current to said capacitive energy storage unit.

2. A system as claimed in claim 1 wherein said capacitive energy storage unit has a large enough capacitive rating to exclusively and solely provide power to all portions of said implantable stimulator during at least an 8 hour period while said stimulator delivers the controlled electric stimulation pulses to targeted tissue.

3. A system as claimed in claim 1 including an external means for replenishing said capacitive power source up to its maximum rated voltage by generating said emf power transmissions near said inductor coil.

4. A system as claimed in claim 3 wherein said external means for replenishing said capacitive energy storage unit up to its maximum rated voltage replenishes said capacitive energy storage unit within two hours or less in the presence of said EMF power transmission near said inductor coil.

5. A system as claimed in claim 3 including means, coupled to said capacitive energy storage unit, for detecting when a voltage, representative of the replenishing current fed to said capacitive energy storage unit, has exceeded a threshold level indicative of a full capacitive power source.

6. A system as claimed in claim 5, said implantable stimulator including means, coupled to said means for detecting, for signaling to said external means for replenishing via specific telemetry code, the completion of the replenishing cycle.

7. A system as claimed in claim 6 including means disposed in said external means for replenishing for detecting said telemetry signal generated by said implantable stimulator to indicate completion of the replenishing cycle.

8. A system as claimed in claim 6 including one of an audible and visual indicator for alerting the user of completion of the replenishing cycle as part of said means for replenishing.

9. A system as claimed in claim 3 wherein said external means for replenishing is powered by one of a primary or rechargeable battery, and is capable of non-invasively transferring the energy from its battery to the capacitive power source within said implanted stimulator utilizing EMF power transmissions within a frequency spectrum from 50 Hertz to 500 KiloHertz.

10. A system as claimed in claim 1 wherein said capacitive energy storage unit is a high value, small size capacitor having a capacitive rating of at least 0.1 farads contained within said implantable stimulator.

11. A system as claimed in claim 10 wherein said capacitor is a single, high value, small size capacitor.

12. A system as claimed in claim 10 wherein said capacitor is a plurality of high value, small size capacitors electrically coupled together in parallel wherein said plurality of capacitors, as a single electronic unit have a capacitive rating of at least 0.1 farads or higher.

13. A system as claimed in claim 1 wherein said small size capacitive energy storage unit has a volumetric size less than 4.0 cubic centimeters, and is contained within said implantable stimulator.

14. A system as claimed in claim 1 wherein said capacitive energy storage unit has an energy storage capacity sufficient to supply power to said implantable stimulator on an exclusive basis over at least an 8 hour period during the continual delivery of stimulation pulses to the targeted tissue.

15. A method of providing, on an exclusive basis, power to an implantable stimulator during at least an 8 hour cycle of substantially continual delivery of one or more electric stimulation pulses to targeted tissue in a controlled manner comprising the steps of:

incorporating and containing a capacitive device in said implantable stimulator, said capacitive device having a capacitive rating of at least 0.1 farads;

capturing at least 5 coulombs of electrical energy in said capacitive device prior to said 8 hour period; and, powering said implantable stimulator, during said 8 hour cycle for the substantially continual delivery of electric stimulation pulses, solely from said capacitive device.

16. A system for delivering electric stimulation pulses, in a controlled manner, to targeted tissue comprising:

an implantable stimulator capable of delivering, in a controlled manner, one or more electric stimulation pulses to targeted tissue;

a power source, contained within said implantable stimulator, sufficient to supply power to said implantable stimulator on an exclusive basis over at least an 8 hour period, said power source including a high value, small size capacitive energy storage unit having a capacitive rating of at least 0.1 farads;

an inductor coil adapted to gather emf power transmissions, a rectifier and a voltage regulator, all electrically coupled to said capacitive energy storage unit and incorporated into said implantable stimulator; and, means, external to said implantable stimulator and not adapted for implantation, for replenishing said capacitive energy storage unit up to its maximum rated voltage by generating said emf power transmission near said inductor coil.

17. A system for delivering electric stimulation pulses as claimed in claim 16 wherein said external means for replenishing is portable and is powered by one of a rechargeable battery and a non-rechargeable battery.

18. A system for delivering electric stimulation pulses as claimed in claim 17 wherein said external means for replenishing includes a transmitting coil which generates emf power transmissions within a frequency spectrum from 50 hertz to 500 kilohertz towards said inductor coil in said implantable stimulator.

19. A system for delivering electric stimulation pulses as claimed in claim 18 wherein said implantable stimulator includes means, coupled to said capacitive energy source, for detecting when a voltage, representative of a replenishing current, fed to said capacitive energy source via said inductor coil, rectifier and regulator, exceeds a threshold level.

20. A system for delivering electric stimulation pulses as claimed in claim 19 wherein said implantable stimulator includes means, coupled to the threshold detector means, for determining and signaling to the external means for replenishing, a completion of a replenishment cycle for said capacitive energy unit.

21. A system for delivering electric stimulation pulses as claimed in claim 20 wherein said external means for replenishing includes means for sensing the completion of replenishment signal from said implant and means, coupled to said sensing means, for alerting the user via one of an audible and a visual indicator of the completion of said replenishing cycle.

22. A system for delivering electric stimulation pulses as claimed in claim 21 wherein said implantable stimulator includes an emf sensitive ON/OFF switch, and means, coupled to said emf sensitive switch, for activating and deactivating said stimulation pulses developed by said implant, and the system includes a user controlled emf source, matched to said emf sensitive switch, which enables the user to non-invasively turn ON and OFF the implant.

23. A system for delivering electric stimulation pulses as claimed in claim 19 wherein said implantable stimulator includes means, coupled to said capacitive energy source, for detecting a low charge voltage when a voltage, present at said capacitive energy source, falls below a low threshold level, and said stimulator includes means, coupled to the low charge voltage means, for reducing the power consumption of said stimulator upon detection of said low charge voltage.

24. A system for delivering electric stimulation pulses as claimed in claim 16 wherein said implantable stimulator includes an emf sensitive ON/OFF switch, and means, coupled to said emf sensitive switch, for activating and deactivating said stimulation pulses developed by said implant, and the system includes a user controlled emf source, matched to said emf sensitive switch, which enables the user to non-invasively turn ON and OFF the implant.

25. A system for delivering electric stimulation pulses as claimed in claim 16 wherein said external means for replenishing includes means for programming said implantable stimulator such that said stimulator delivers electric stimulation pulses to said targeted tissue in a manner dependent upon the stimulation program.

* * * * *